United States Patent [19]
Yates et al.

[11] Patent Number: 5,688,270
[45] Date of Patent: *Nov. 18, 1997

[54] ELECTROSURGICAL HEMOSTATIC DEVICE WITH RECESSED AND/OR OFFSET ELECTRODES

[75] Inventors: David C. Yates, West Chester; James Voegele, Cincinnati, both of Ohio

[73] Assignee: Ethicon Endo-Surgery,Inc., Cincinnati, Ohio

[*] Notice: The term of this patent shall not extend beyond the expiration date of Pat. No. 5,403,312.

[21] Appl. No.: 374,012

[22] Filed: Jan. 18, 1995

Related U.S. Application Data

[63] Continuation-in-part of Ser. No. 95,797, Jul. 22, 1993, Pat. No. 5,403,312, and a continuation-in-part of Ser. No. 96,154, Jul. 22, 1993, abandoned.

[51] Int. Cl.$^6$ .................................................. A61B 17/39
[52] U.S. Cl. ................................. 606/51; 606/50; 606/49; 606/46; 606/41
[58] Field of Search ........................... 606/37–42, 45–52, 606/205–209, 142, 143

[56] References Cited

U.S. PATENT DOCUMENTS

| | | | |
|---|---|---|---|
| 2,031,682 | 2/1936 | Wappler et al. | 606/46 |
| 4,608,981 | 9/1986 | Rothfuss et al. . | |
| 4,633,874 | 1/1987 | Chow et al. . | |
| 4,655,216 | 4/1987 | Tischer | 606/46 |
| 4,671,274 | 6/1987 | Sorochenko . | |
| 4,985,030 | 1/1991 | Melzer et al. . | |
| 5,057,107 | 10/1991 | Parins et al. . | |
| 5,085,659 | 2/1992 | Rydell . | |
| 5,098,431 | 3/1992 | Rydell . | |
| 5,104,025 | 4/1992 | Main et al. . | |
| 5,151,102 | 9/1992 | Kamiyama et al. | 606/51 |
| 5,171,255 | 12/1992 | Rydell . | |
| 5,190,541 | 3/1993 | Abele et al. . | |
| 5,201,900 | 4/1993 | Nardella . | |
| 5,207,691 | 5/1993 | Nardella . | |
| 5,217,458 | 6/1993 | Parins . | |
| 5,290,286 | 3/1994 | Parins . | |
| 5,389,098 | 2/1995 | Tsuruta et al. . | |
| 5,417,687 | 5/1995 | Nardella et al. . | |
| 5,443,463 | 8/1995 | Stern et al. | 606/51 |

FOREIGN PATENT DOCUMENTS

| | | |
|---|---|---|
| 0 210 125 A1 | 7/1985 | European Pat. Off. . |
| 0 589 453 A2 | 9/1992 | European Pat. Off. . |
| 0 596 436 A1 | 11/1992 | European Pat. Off. . |
| 0 517 244 | 12/1992 | European Pat. Off. . |
| 0 518 230 | 12/1992 | European Pat. Off. . |
| 93/08754 | 5/1993 | WIPO . |
| WO 93/08754 | 5/1993 | WIPO . |
| WO 94/24949 | 11/1994 | WIPO . |
| WO 94/24951 | 11/1994 | WIPO . |

OTHER PUBLICATIONS

Automatically Controlled Bipolar Electrocoagulation–"COA–COMP", Neurosurg. Ref. (1984) 187–190; B. Vallofors and B. Bergdahl.

Instrument for Stomach Resection and Bowel Anastomosis Used During Closed Procedures, Department of Surgery of Mukachevo City Hospital, N.G. Vittenberger, Jan.–Feb. 1958, First Issue (the 211th).

*Primary Examiner*—Jennifer Bahr
*Assistant Examiner*—Michael Peffley

[57] ABSTRACT

An electrosurgical instrument is provided for cauterization and/or welding of tissue of varying impedances, thicknesses and vascularity especially in the performance of endoscopic procedures. The instrument compresses the tissue between an electrode associated with a first pole of a bipolar energy source located on one interfacing surface off a first element, and a second interfacing surface of a second element. The first and second elements are used to engage and compress tissue between the first and second interfacing surfaces. A second electrode associated with a second pole is located one of the two interfacing surfaces. The first electrode is either recessed into the first tissue contacting surface and/or offset from the second electrode on the same or opposing surfaces. A preferred application of the invention is in a cutting instrument wherein a hemostatic line is formed along a cut line using RF energy.

32 Claims, 14 Drawing Sheets

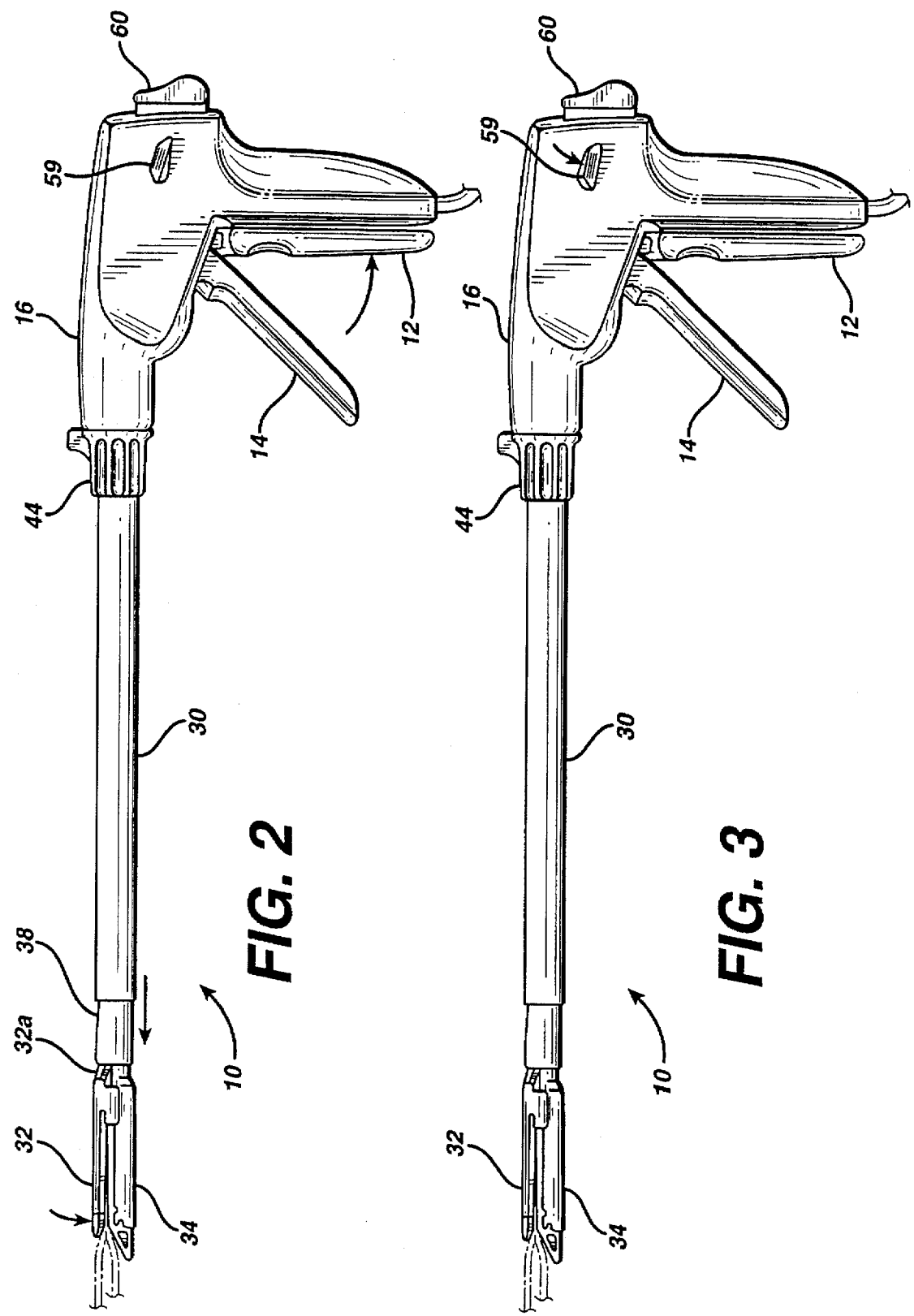

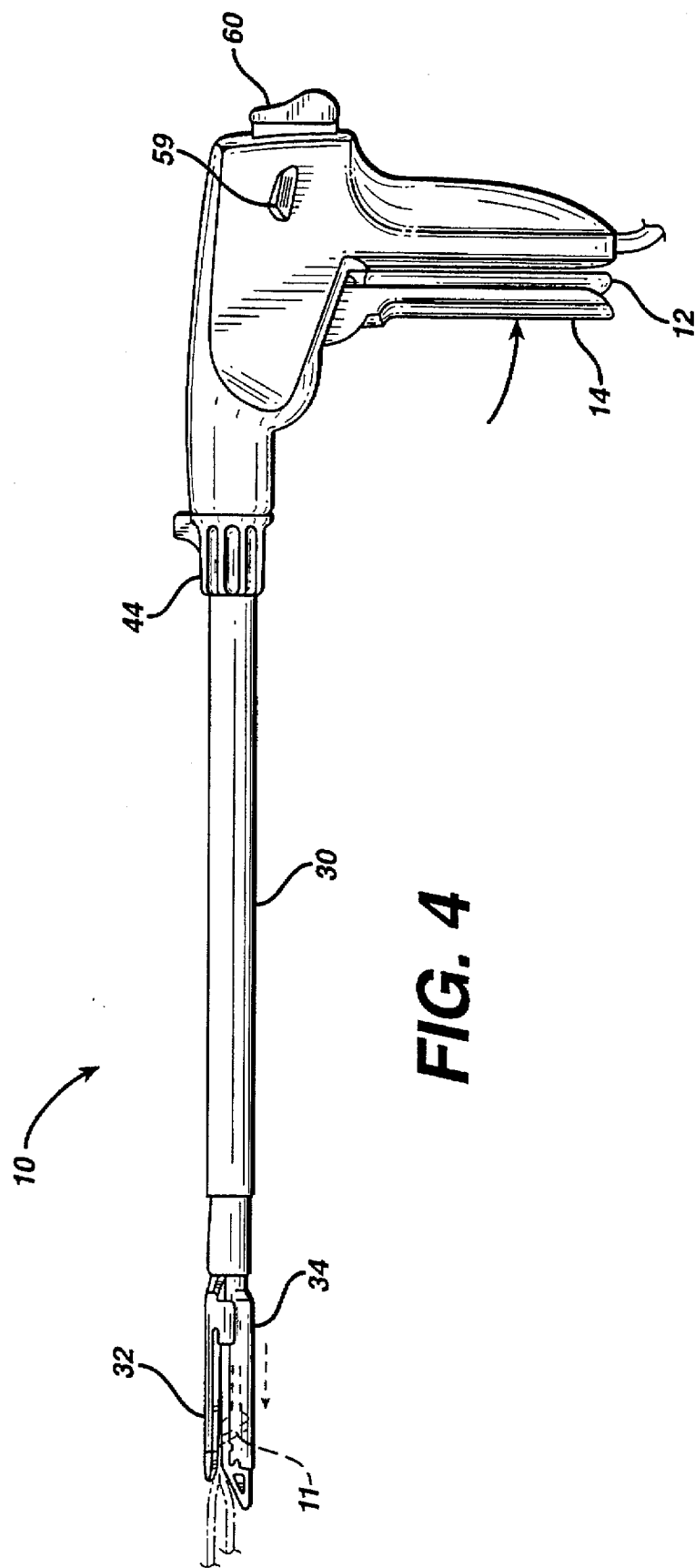

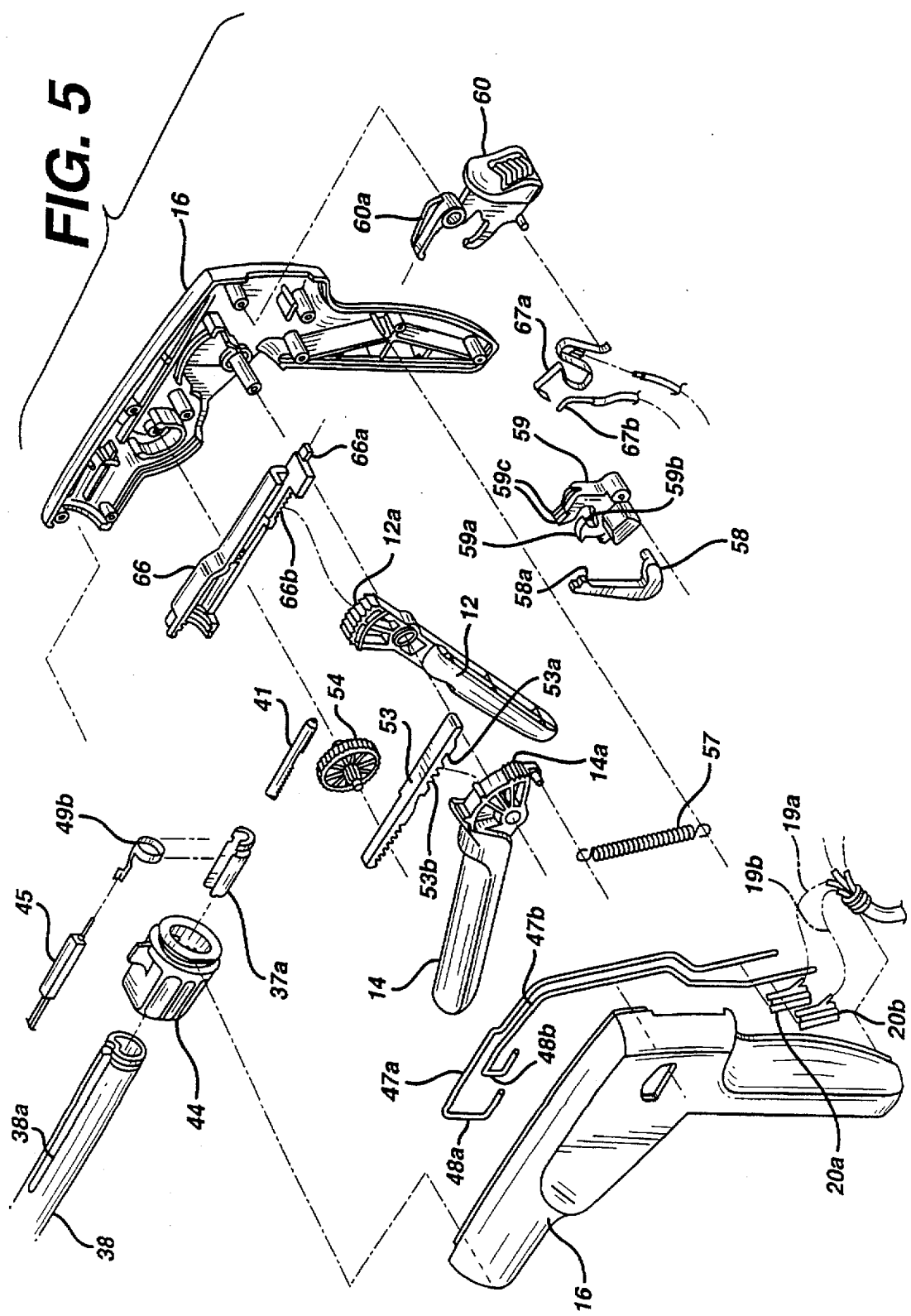

ELECTROSURGICAL HEMOSTATIC DEVICE WITH RECESSED AND/OR OFFSET ELECTRODES

This is a continuation-in-part to U.S. Application Ser. No. 08/095,797, filed on Jul. 22, 1993, now U.S. Pat. No. 5,403,312, and U.S. application Ser. No. 08/096,154, filed on Jul. 22, 1993, (both abandoned) both of which are incorporated herein by reference.

FIELD OF THE INVENTION

This invention relates to an electrosurgical instrument for cauterization, coagulation and/or tissue welding in the performance of surgical procedures, especially endoscopic procedures.

BACKGROUND OF THE INVENTION

Surgical procedures requiring cutting of tissue can cause bleeding at the site of the cutting. Various techniques have been adapted to control bleeding with varying degrees of success such as, for example, suturing, applying clips to blood vessels, and stapling, as well as electrocautery and other tissue heating techniques. Advances in tissue joining or welding, tissue repair and wound closure also have permitted surgical procedures previously not possible or too risky.

Surgical staplers have been used for tissue security, joining, and approximation, and to provide hemostasis in conjunction with tissue cutting. Such devices include, for example, linear and circular cutting and stapling instruments. Typically, a linear cutter has parallel rows of staples with a slot for a cutting means to travel between the rows of staples. This type of surgical stapler secures tissue for improved cutting, joins layers of tissue, and provides hemostasis by applying parallel rows of staples to layers of surrounding tissue as the cutting means cuts between the parallel rows.

Electrocautery devices have been used for effecting improved hemostasis by heating tissue and blood vessels to cause coagulation or cauterization. Monopolar devices utilize one electrode associated with a cutting or cauterizing instrument and a remote return electrode, usually adhered externally to the patient. More recently, bipolar instruments have been used because the cauterizing current is generally limited to tissue between two electrodes of a tissue treating portion of an instrument.

Bipolar forceps have been used for cutting and/or coagulation in various procedures. Generally, bipolar forceps grasp tissue between two poles and apply electrical current through the grasped tissue. Bipolar forceps, however, have certain drawbacks, some of which include the tendency of the current to arc between poles when tissue is thin or the forceps to short when the poles of the forceps touch. The use of forceps for coagulation is also very technique dependent and the forceps are not adapted to simultaneously cauterize a larger area of tissue. Furthermore, forceps tend to cause areas of thermal spread, i.e., dissipation of heat outside of area defined by grasping or engaging surfaces of the forceps.

SUMMARY OF THE INVENTION

It is therefore an object of the present invention to provide a hemostatic electrosurgical instrument which can efficiently provide hemostasis in multiple tissue types and thicknesses, e.g., in fleshy or vascular tissue areas, and high, low or combination impedance tissues. Hemostasis is used herein to mean generally the arresting of bleeding including by coagulation, cauterization and/or tissue joining or welding.

It is another object of the invention to provide an electrosurgical hemostatic device which is capable of being used to simultaneously cauterize or weld a relatively larger area or length of tissue than in previously known devices.

Another object of the invention is to provide a controlled current delivery path by arranging offset and/or recessed electrodes to provide a desired current path, preferably through a zone of high tissue compression. Offset electrodes are defined herein to mean electrodes which are not diametrically opposed to each other with respect to interfacing surfaces. Recessed electrodes are defined herein to mean electrodes which are recessed from a tissue contacting plane; a tissue contacting plane may be defined by one of the interfacing or opposing surfaces.

It is another object of the invention to provide an electrosurgery device having one or more elongated or bar electrodes.

Another object of the invention to is provide a hemostatic means for providing a line of coagulation adjacent to a cutting path of a cutting means for dividing tissue.

Another object of the invention is to provide a cutting and stapling device with an electrocautery means for tissue welding or cauterization along a cutting path.

These and other objects of the invention are described in an electrosurgical device having an end effector with opposing interfacing surfaces for engaging tissue therebetween, and two electrically opposite electrodes, corresponding to electrically opposite poles, each electrode located on one or both of the opposing surfaces. The electrodes are offset from each other with respect to interfacing surfaces, i.e., they are offset from each other so that they are not diametrically opposed from each other on an interfacing surface or surfaces. If the electrodes are on the same surface, they are separated from each other with an insulating material or an insulator (which may include an air gap) which electrically isolates the electrodes.

An electrosurgical instrument of a preferred embodiment compresses tissue in a compression zone between a first interfacing surface and a second interfacing surface and applies electrical energy through the compression zone. The first interfacing surface is comprised of: a first electrode corresponding to a first pole of a bipolar energy source and a second electrode corresponding to a second pole of a bipolar energy source. The second electrode is located on the same or opposite interfacing surface as the first electrode. In a preferred embodiment, the compression zone is an area defined by a compression ridge on one of the interfacing surfaces which compresses the tissue against the other interfacing surface. Also, there may be a compression ridge on both interfacing surfaces. A coagulation zone is defined by the first electrode, the second electrode, and an insulator insulating the first electrode from the second electrode. This arrangement electrically isolates the two poles and enables the current path between the first and second electrodes to cross through a desired area of compressed tissue.

It is believed that the tissue compression normalizes tissue impedance by reducing structural differences in tissue which can cause impedance differences. Compression also stops significant blood flow and squeezes out blood and other interstitial fluids which act as a heat sink, particularly when flowing through veins arteries and other vessels. It is further believed that high compression causes a higher current density to be delivered through compressed tissue in contact with an energy delivering electrode. Thus, it is believed that compression optimizes delivery of energy to tissue in part by preventing excessive thermal dissipation due to blood flow, dissipation through surrounding boundaries, and by enabling quick delivery of a higher current density to a controlled area of tissue.

The arrangement of the electrodes is important to ensure that the current passing between the two poles passes though the compression zone. Also the invention provides for offsetting, i.e., insulating or isolating of the electrically opposite electrodes from each other with respect to the interfacing surfaces of the instrument and/or recessing one or more tissue contacting electrodes within an instrument so that the recessed electrode contacts tissue in a zone of high compression while permitting tissue compression without shorting of the instrument poles or electrical arcing common in bipolar instruments.

Thus, the tissue compression and the arrangement of the electrodes permit more efficient cauterization and offer the advantage of achieving hemostasis in a wide range of tissue impedance, thickness and vascularity.

The present invention also provides a device capable of coagulating a line or path of tissue along or lateral to a cut line or a cutting path. In one embodiment, the first electrode and second electrodes each comprise an elongated electrode each on opposite sides and laterally adjacent an insulator forming a ridge to compress the tissue to be cauterized.

In one preferred embodiment, a cutting means for cutting tissue is incorporated into the device and the device provides hemostatic lines adjacent to the path of the cutting means. Of course, cutting may occur at anytime either before, during or after cauterization or welding. In variations of this embodiment, stapling means may be provided on one or both sides of the cutting path.

In one embodiment, an indicator means communicates to the user that the tissue has been cauterized to a desired or predetermined degree.

In one embodiment, electrosurgical energy is applied in conjunction with application of one or more tissue fasteners such as, for example, staples, clips, absorbable fasteners etc., using an applier to apply the fastener, such as a driver to drive staples into tissue.

In another embodiment, the coagulation is completed prior to any mechanical cutting, i.e., actuation of the cutting means. If an indicator means is used, once tissue is coagulated, the cutting means may be actuated to cut between the elongated bar electrodes while the rows of staples are applied to the tissue.

In another embodiment, the hemostatic device is incorporated into a linear cutter similar to a linear cutting mechanical stapler. In this embodiment the hemostatic device comprises two elongated electrode bars and a slot for a cutting means to cut tissue engaged by the end effector of the device. Optionally, one or more rows of staples may be provided on each side of the slot and bars to provide mechanical tissue security or approximation during the healing process. In operation, tissue is clamped between two jaws. Electrical energy in the form of radio frequency current is applied to the compressed tissue to cauterize the tissue. Other cutting and stapling instruments may be used as well, such as, for example, cutting and an interluminal circular cutting instrument.

Another embodiment provides a means for detecting abnormal impedances or other electrical parameters which are out of a predetermined range. For example, the means for detecting may be used to indicate when the instrument has been applied to tissue exhibiting impedances out of range for anticipated good coagulation. It may also be used for detecting other instrument abnormalities. It is possible to detect the abnormal condition, for example, by using comparisons of normal ranges of initial tissue impedances in the interface electronics. This could be sensed in the first few milliseconds of the application of RF energy and would not present a significant therapeutic dose of energy or by a low voltage signal used prior to delivering therapeutic energy. A warning mechanism may be used to warn the user when the impedance is out of range. Upon repositioning of the instrument, the same measurement criteria would apply and if the tissue impedance was again out of range, the user would again be warned. This process would continue until the normal impedance range was satisfied and good coagulation could be anticipated.

These and other objects of the invention will be better understood from the following attached Detailed Description of the Drawings, when taken in conjunction with the Detailed Description of the invention.

DETAILED DESCRIPTION OF THE DRAWINGS

FIG. 2 is a side elevational view of the embodiment of FIG. 1 shown in a closed, clamped position, before cutting or stapling;

FIG. 3 is a side elevational view of the embodiment of FIG. 2 shown as RF energy is applied to tissue;

FIG. 4 is a side elevational view similar to FIG. 3 shown after RF energy has been applied and the tissue has been stapled and cut;

FIG. 5 is an exploded perspective view of the proximal handle portion of the instrument of FIG. 1;

DETAILED DESCRIPTION OF THE PREFERRED EMBODIMENTS

While the present invention is generally applicable to a variety of electrosurgical instruments including monopolar, bipolar and multipolar (i.e., including two or more therapeutic electrodes providing energy in waveforms as measured from any pole to any other pole as having a phasic relationship), and both conventional and endoscopic, it will be described herein with reference to an endoscopic bipolar linear cutting and stapling instrument.

Operation of linear cutting and stapling instruments are known in the art and are discussed, for example, in U.S. Pat. Nos. 4,608,981, 4,633,874, and U.S. application Ser. No. 07/917,636 incorporated herein by reference.

Figure 1:
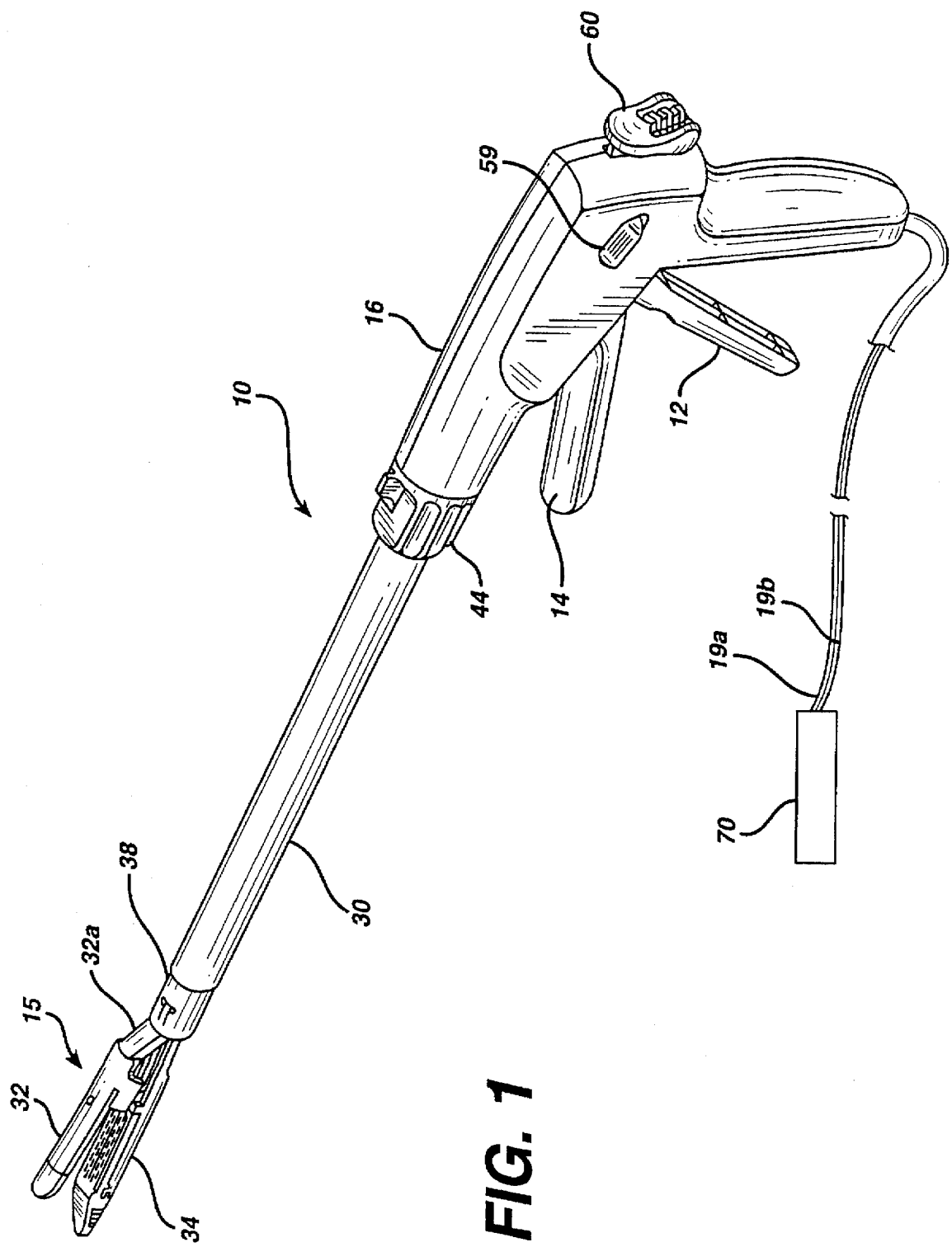
FIG. 1 is a perspective view of an endoscopic electrosurgical instrument of one embodiment of the present invention.
Figure 6:
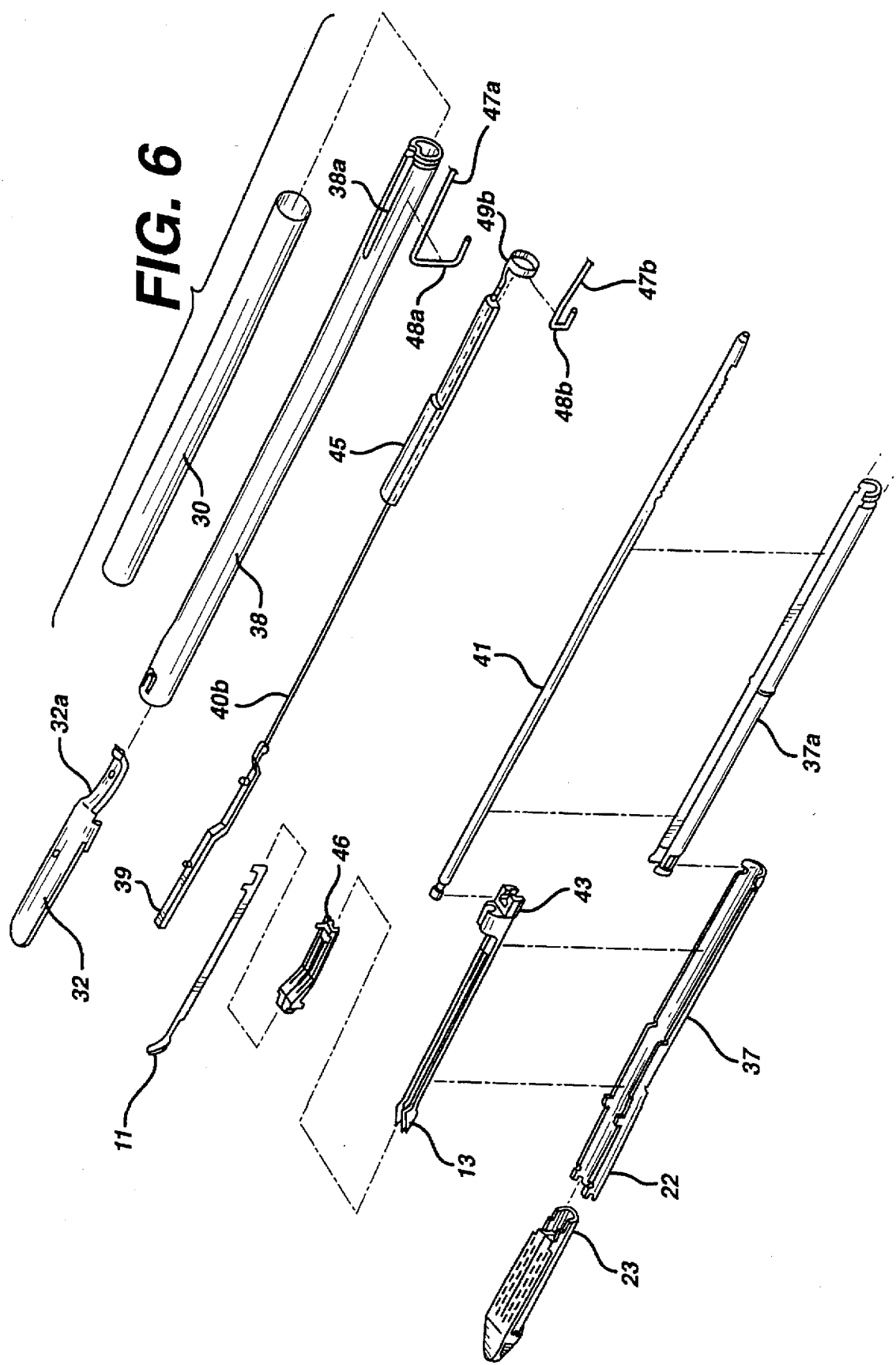
FIG. 6 is an exploded perspective view of the intermediate and distal portion of the instrument of FIG. 1.
Figure 7:
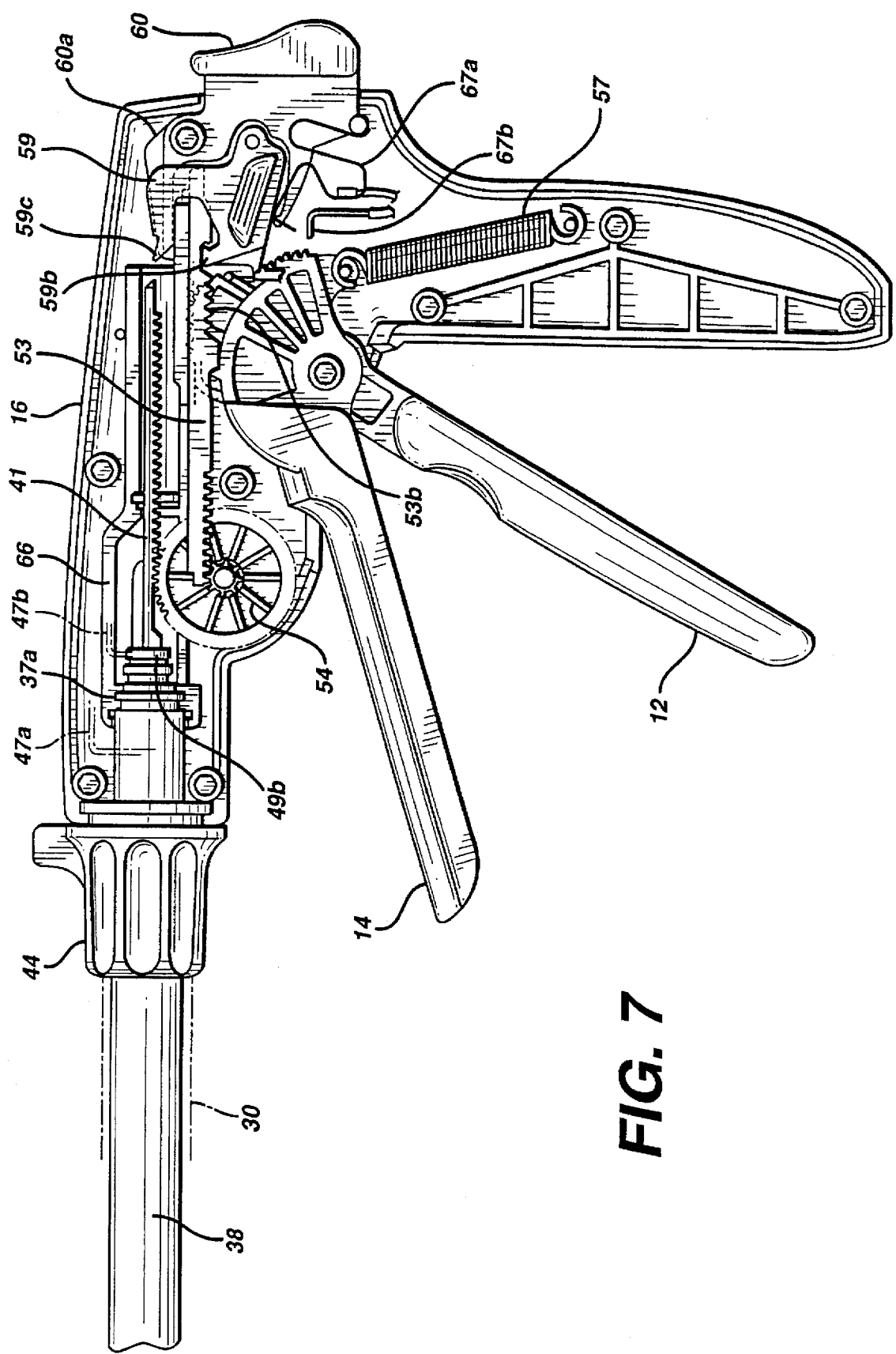
FIG. 7 is a side elevational view of the proximal handle portion in a first, open position of the instrument of FIG. 1, shown with the left side handle cover and wireforms removed.
Figure 8:
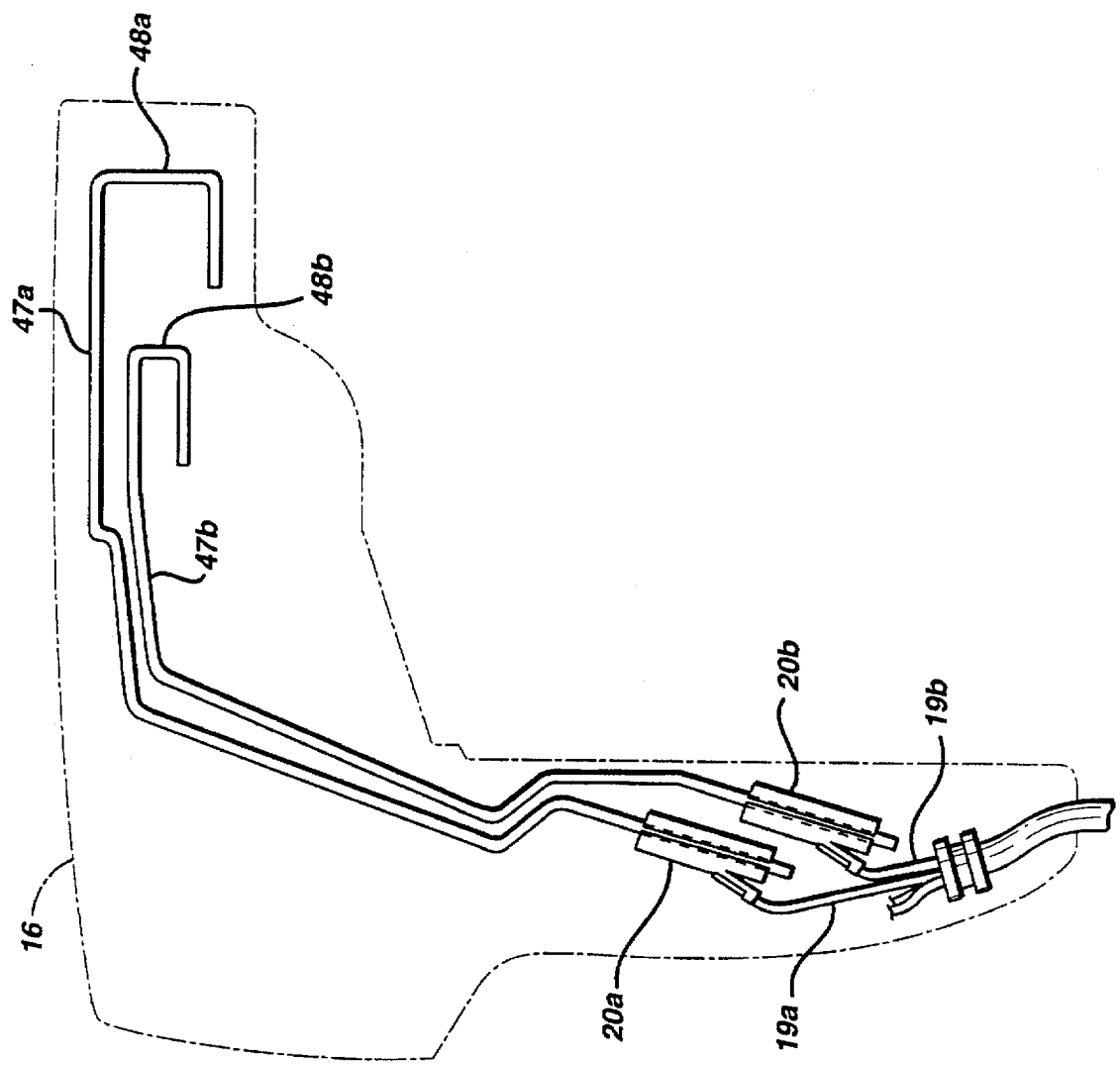
FIG. 8 is an elevational view of the inside of the left side handle portion showing the location of the wireforms and connectors used in the present invention.
Figure 9:
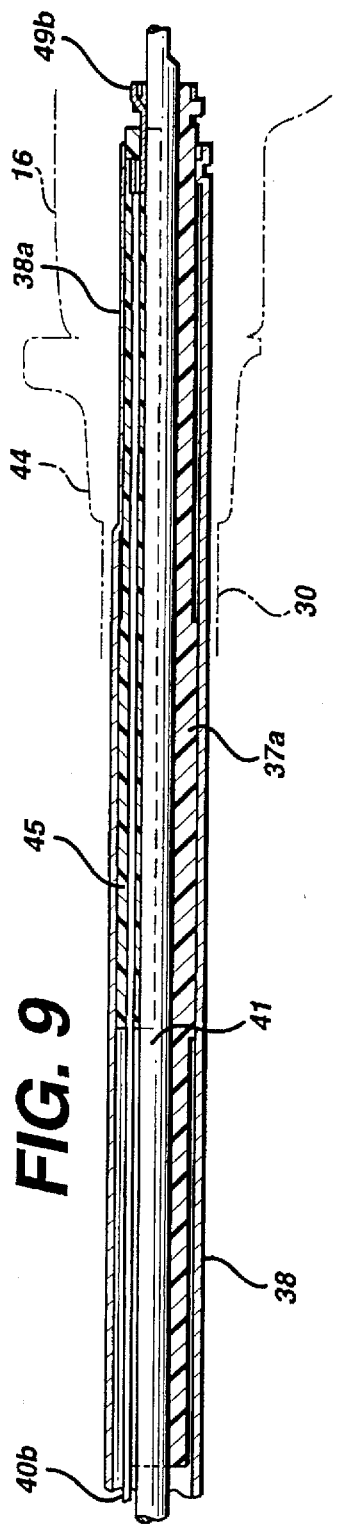
FIG. 9 is a longitudinal cross-sectional view of the intermediate portion of the instrument.
Figure 10:
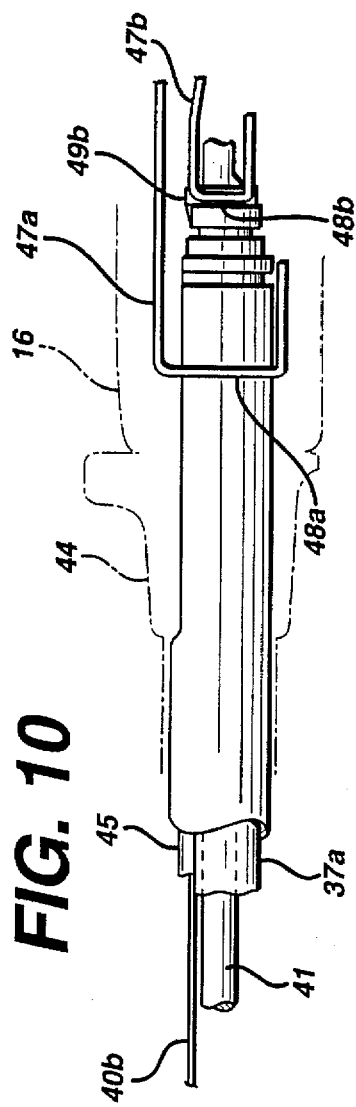
FIG. 10 is an elevational view of the proximal end of the intermediate portion showing the contact of the wireforms to their respective contact positions.
Figure 11A:
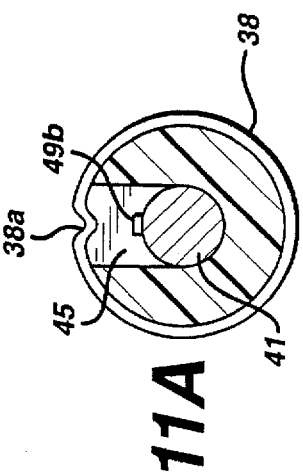
FIG. 11a is a transverse cross sectional view taken along the lines 11a—11a of FIG. 11.
Figure 11:
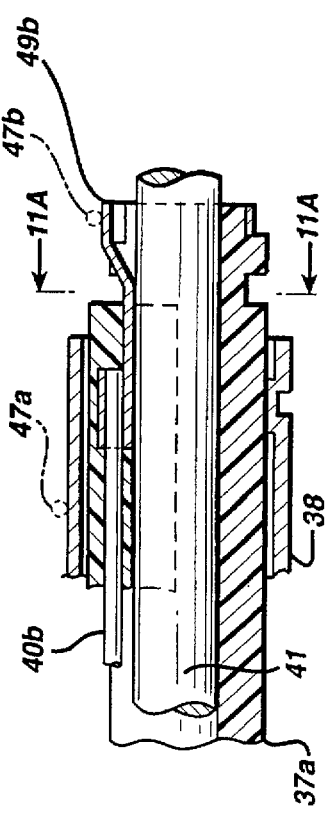
FIG. 11 is an enlarged cross-sectional view of the proximal end of the intermediate portion of the instrument.
Figure 13:
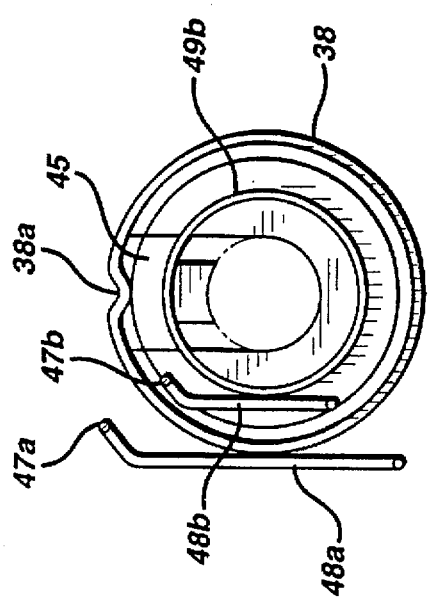
FIG. 13 is an end view of FIG. 11 showing a slight bias in the wireforms allowing for pressure of the wireforms onto their respective contact positions.
Figure 12:
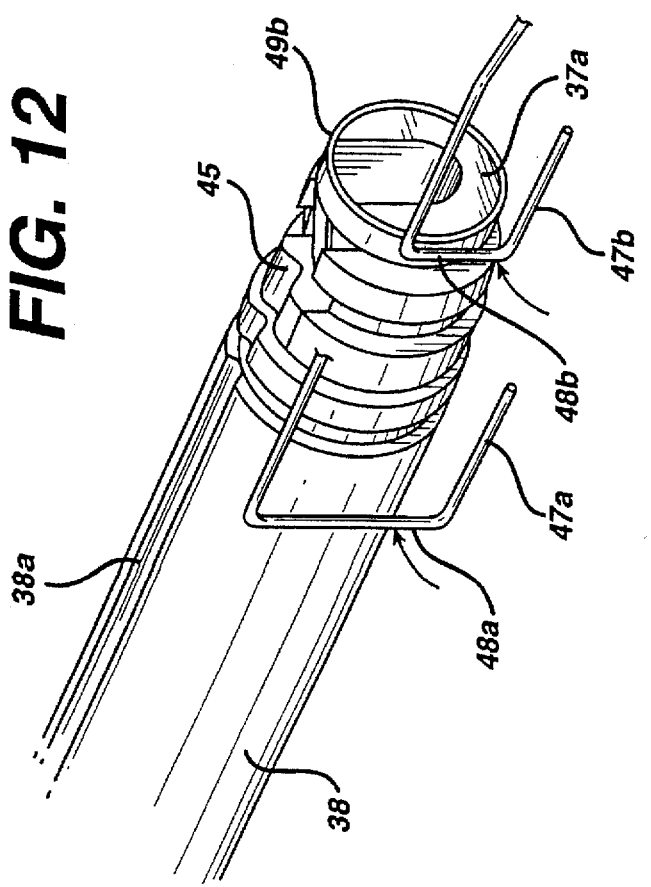
FIG. 12 is a perspective view showing the wireforms contacting their respective contact position.
Figure 14:
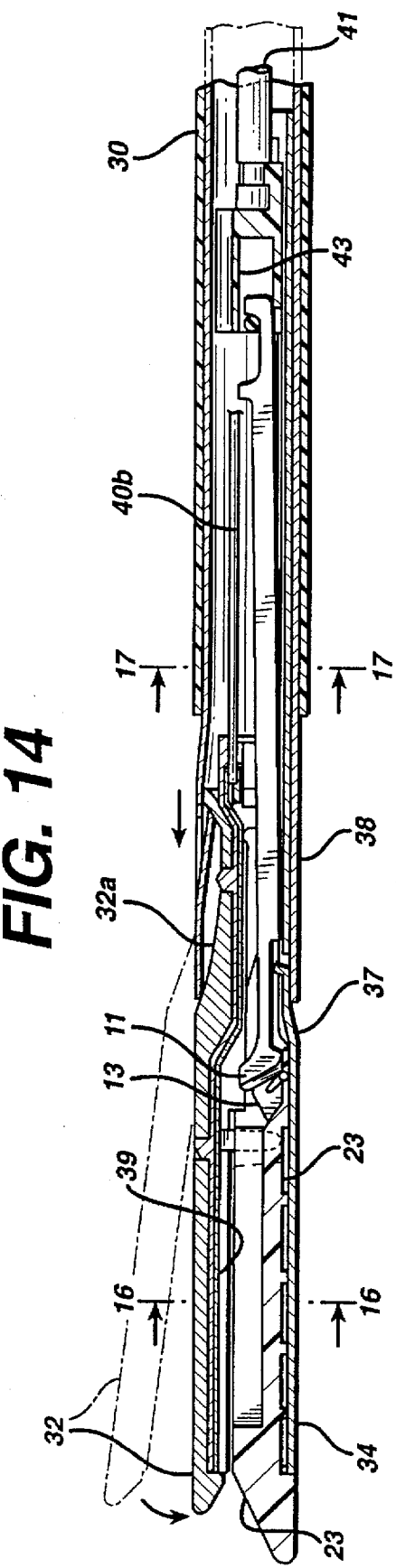
FIG. 14 is a longitudinal cross-sectional view of the distal end of the instrument of FIG. 1 shown in a closed and clamped position.
Figure 15:
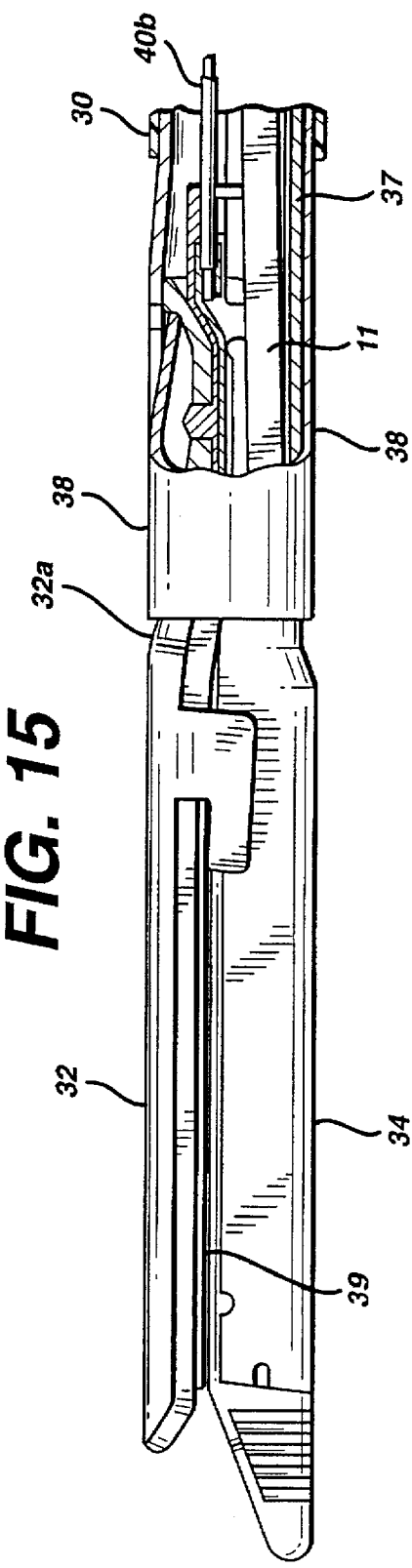
FIG. 15 is an enlarged partial cross-sectional view of the distal portion of FIG. 13.

Referring now to FIGS. 1–17 there is illustrated an instrument of the present invention to be used in conjunction with an impedance feedback device. An endoscopic linear cutting and stapling instrument 10 is shown having a housing 16 coupled to a sheath 30 with a lumen extending therethrough and an end effector 15 extending from the distal end of the sheath 30. The end effector 15 comprises first and second elements which are comprised of interfacing jaw members 32, 34. Jaw member 32 is movably secured to jaw member 34. The housing 16 has a clamping trigger 12 for closing jaw members 32, 34, an RF switch detente arm 58 and electrical switch contacts 67a, 67b, coupled to an electrical switch 59 for turning on RF energy, and a firing trigger 14 for advancing the cutting element 11 through tissue and wedge 13 for applying staples 17. Jaw members 32, 34 are shown in an unclamped position in FIG. 1; in a clamped position prior to application of electrosurgical energy and prior to cutting and stapling in FIG. 2; in a clamped position after application of electrosurgical energy and prior to cutting and stapling in FIG. 3; and in a clamped position after cutting and stapling in FIG. 4.

Figure 16:
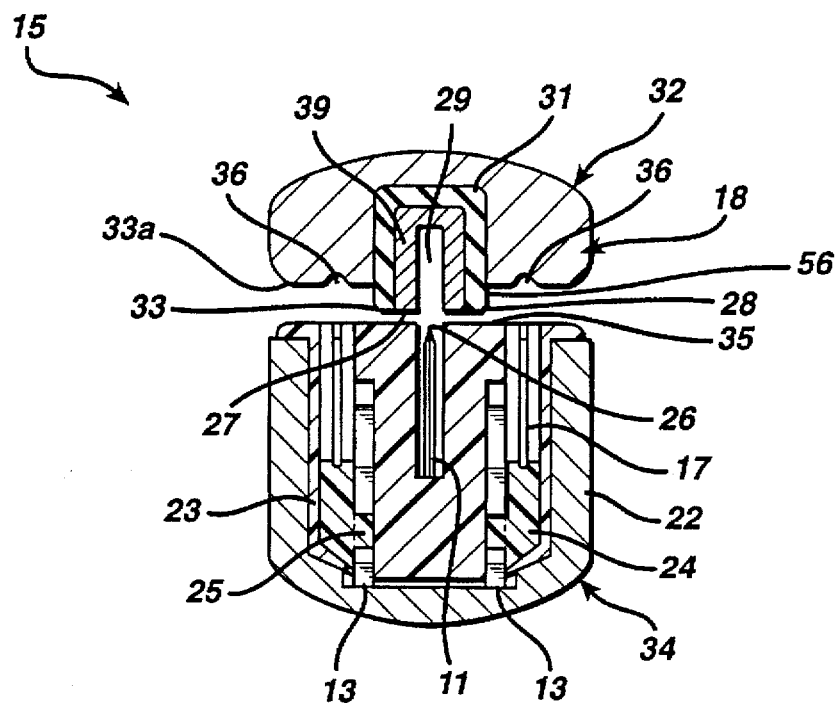
FIG. 16 is a transverse cross-sectional view taken along line 16—16 of FIG. 14.
Figure 17:
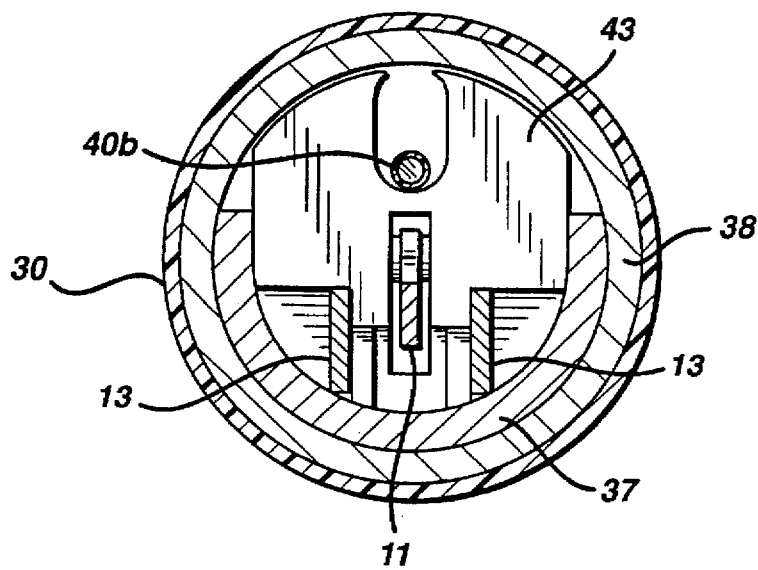
FIG. 17 is a transverse cross-sectional view taken along line 17—17 of FIG. 14.

Jaw member 32 comprises an anvil 18, U-shaped therapeutic electrode 39 extending along the length of the jaw 32, and a U-shaped insulating material 31 surrounding the outside of the therapeutic electrode 39. Jaw member 32 has an inner surface 33 which substantially faces an inner surface 35 of jaw member 34. The U-shaped electrode 39 comprises two electrically communicating electrode bars 27, 28 forming a first pole and located on and extending substantially along the length of the inner surface 33. The U-shaped electrode 39 is comprised of a conductor, such as, aluminum or surgical grade stainless steel. The U-shaped insulator is preferably formed of a polymer such as polyphenyleneoxide. The bars 27, 28 are separated by a knife channel 29 extending longitudinally through the middle of the electrode 39. Pockets 36 located on anvil 18 for receiving staple ends are located along the inner surface 33, along the length and outside of bars 27, 28, to form a row of staples on each side of electrode 39. The electrode bars 27, 28 and insulating material 31 form a ridge 56 extending out relative to an anvil portion 33a of the inner surface 33 (FIG. 16). The electrode 39 acts as a first pole of a bipolar tissue treatment or therapeutic system. The anvil 18 is formed of an electrically conductive material and acts as a second therapeutic electrode of the bipolar treatment or therapeutic system, the anvil being electrically opposite of the treatment electrode 39. The anvil 18 is electrically isolated from electrode 39 by the U-shaped insulating material 31.

Jaw member 34 comprises a cartridge channel 22 and a cartridge 23 releasably inserted into the cartridge channel 22. The cartridge 23 includes a track 25 for wedge 13, a knife channel 26 extending longitudinally through the center of the cartridge 23, a series of drivers 24 extending into the track 25 and staples 17 arranged in two sets of single rows.

The sheath 30 is formed of an insulative material and has an electrically conductive closure tube 38 extending through its lumen. In a preferred embodiment, the closure tube 38 acts as a jaw closure tube and as an electrical contact. A channel retainer 37a extends from the proximal end of the closure tube 38 and is secured to channel 37 which there extends distally through the remainder of the closure tube 38 to form jaw member 34. The channel 37 includes cartridge channel 22 extending distally from the closure tube 38.

The body 16 has a clamping trigger 12 for advancing the closure tube 38 to close the jaws 32, 34 towards each other engaging tissue therebetween. Rotation of the clamping trigger 12 causes the closure tube 38 to advance co-axially through the sheath 30 over a camming surface 32a of jaw 32 to close the jaws 32, 34 onto tissue situated between the jaws 32, 34.

The channel retainer 37a guides co-axial movement of a drive rod 41 within the channel 37. The drive rod 41 is advanced by the rotation of the firing trigger 14 as described in more detail below. The driving rod 41 is coupled on its distal end to a block 43. The block 43 is coupled to a cutting means 11 and a staple driving wedge 13, which the drive rod 41 advances by way of the block 43 into the end effector 15. A wedge guide 46 is used to guide wedge 13 into track 25. Jaw member 32 is secured by way of the channel 37 to the jaw member 34.

When the drive rod 41 advances the cutting element 11, the cutting element 11 advances through the knife channel 26 in between the bars 27, 28 to cut tissue engaged by jaws 32, 34 when the tissue has been cauterized. Thus, the cut line is medial to the coagulation lines formed by the bar electrodes 27, 28. The drive rod 41 simultaneously advances the block 43 and thus the wedge 13 which drives the drivers 24 into the staples 17 causing the staples 17 to fire through tissue and into the pockets 36 of the anvil 18. Staples 17 are applied in single longitudinal rows on each side of the cutting element 11 as the cutting element 11 cuts the tissue.

A knob 44 located on the distal end of the body 16 rotates the closure tube 38, channel retainer 37a, channel 37 and end effector 15 which are directly or indirectly coupled to the knob 44 so that the knob 44 may be used for rotational placement of the end effector jaws 32, 34. The knob 44 includes a peg (not shown) which fits into and engages indentation 38a closure tube 38. Closure tube 38 is fitted at its proximal end, into the housing 16.

Electrical energy is supplied to the electrode 39 and anvil 18, 70 (FIG. 20) through connections such as those described below, or other connections means, such as, for example, like those described in parent application Ser. No. 08/095,797, incorporated herein by reference. The generator 70 is user controlled by way of RF switch 59 located in the housing 16.

Wires 19a and 19b extend into the body 16 of the instrument and deliver energy to electrodes 39, 18 respectively. Wires 19a, 19b are coupled to low impedance contact elements 20a, 20b respectively and contact elements 20a, 20b are coupled to wireforms 47a, 47b respectively. Wireforms 47a, 47b are exposed at their distal ends 48a, 48b. Wireforms 47a and 47b are biased respectively towards closure tube 38 and contact ring 49b located on the proximal end of channel retainer 37a, so as to make electrical contact with the closure tube 38 and ring 49b respectively.

Wire 19a delivers electrical current to the anvil 18 by way of first wire form 47a which contacts electrically conductive closure tube 38 which contacts electrically conductive anvil 18 as closure tube 38 closes jaws 32, 34.

Wire 19b delivers electrical current to the electrode 39 through second wire form 47b which contacts contact ring 49b coupled to wire 40b extending through the closure tube 38 to the electrode 39.

The closure tube 38 and ring contact 49b permit the knob 44 to rotate while contact is maintained between closure tube 38, ring 49b, and wireforms 47a, 47b, respectively. The ring 49b is electrically insulated from the closure tube 38.

Wire 40b extends through seal 45 which fits into channel retainer 37a, which fits into closure tube 38.

Clamping trigger 12 includes gear teeth 12a which movably engage with teeth 66b of yoke 66. Yoke 66 is coupled on its distal end to the closure tube 38. When clamping trigger 12 is actuated, the gear teeth 12a engage with teeth 66b in yoke 66 causing the yoke 66 to advance distally. Closure tube 38 closes jaws 32, 34 as it advances over camming surface 32a of jaw 32.

The RF switch 59 is rotated to switch on RF energy to be supplied to the therapeutic electrodes. When the RF switch 59 is rotated, detente protrusion 59a on the switch 59 hooks under detente protrusion 58a on detente arm 58, preventing the switch 59 from deactivating RF energy unless the RF switch 59 is manually rotated back to its original position. The RF energy may also be turned off electrically.

Switch 59 has a moveable contact 67a and a stationary contact 67b. The moveable contact 67a rotates with switch 59 to contact stationary contact 67b when switch is on.

Ledge 60a of release button 60 is engaged with the proximal end of the yoke 66 adjacent step ledge 66a on proximal end of yoke 66. When the yoke 66 is advanced by the clamping trigger 12, the ledge 60a rotates down behind proximal end of yoke 66, thereby preventing yoke 66 from retracting until release button 60 has been pressed. Thus the jaws 32, 34 will remain in a closed position until a user releases the jaws 32, 34 with release button 60.

The switch 59 includes fingers 59c which sit just above proximal end of yoke 66. The ledge 60a of the release button 60 fits in between fingers 59c. The RF switch 59 cannot be activated, i.e., rotated forward, until the yoke 66 has been advanced distally so that fingers 59c of switch 59 are free to rotate behind proximal end of yoke 66.

The switch 59 also includes a lower hook 59b which engages groove 53a of firing rack 53. Firing rack 53 includes gear teeth 53b which are engaged by gear teeth 14a of firing trigger 15. The firing rack 53 is coupled on its distal end to pinion gear 54 which in turn engages the drive rod 41.

When the firing trigger 14 is pulled, the fire rack 53 is advanced distally to rotate pinion 54 which advances the driving rod 41 distally to actuate the cutting element 11 and to drive staples 17 into tissue engaged by the end effector 15.

The firing rack 53 cannot advance however until the lower hook 59b of the RF switch is disengaged from the groove 53a of the firing rack 53. This occurs only when the RF switch 59 has been activated.

Thus, the presently described device includes a lockout device or devices for preventing application of RF energy, staples or knife actuation until the jaws 32, 34 have been closed. The lockout device(s) require the proper sequence is followed as illustrated in FIGS. 1-4, i.e., jaw closure, followed by application of RF energy, followed by staple application and cutting element actuation. It also provides a detented RF switch so that RF energy is continuously applied until the switch 59 is manually released or until the RF energy is switched off, e.g., by an electrical feedback control signal to the generator 70.

The closure trigger 12 and firing trigger 14 are interlocked and a spring 57 is mechanically coupled to both triggers 12, 14.

When tissue is engaged between clamped jaw members 32, 34, and RF energy has been applied, the firing trigger 14 located on housing 16 may be actuated to advance a cutting element 11 through the engaged tissue to cut the tissue. Simultaneously, when the firing trigger 14 is actuated, the wedge 13 is advanced through the track 25 causing the drivers to 24 to displace towards the staples 17, thereby driving the staples 17 through tissue and into anvil pockets 36.

In one embodiment, the cartridge provides multifire stapling capabilities by having single rows of staples, as opposed to the convention double row of staples of the cartridges in the laparoscopic stapling and cutting devices presently in use. In order to provide better hemostasis, this type of stapler was designed to provide a double row of staples for each parallel row. Because of the size of the space necessary to contain the double row of staples, a refireable cartridge with stacked staples has not been preferred because of the additional space required for stacking staples. In the multifire stapling embodiment a single row of staples is used. Using a single row of staples permits stacking of staples in the space previously occupied by the second row of staples, providing multifire capabilities. The device of the present may however, if desired, include double, triple, etc., staple rows. Also, in a further embodiment, no staples are required and the electrical coagulation lines provide the necessary hemostasis or tissue welding effect. A cartridge is defined herein to mean a staple containing mechanism.

A preferred embodiment of the present invention includes a feedback system designed to indicate when a desired or predetermined tissue effect has occurred. An audible, visible, tactile, or other feedback system may be used to indicate when sufficient cauterization has occurred at which point the RF energy may be turned off. In a particular embodiment, the feedback system measure one or more electrical parameters of the system, e.g., the electrical impedance of the tissue to which the electrical energy is applied, to determine tissue characteristics, e.g., coagulation complete. An example of such a feedback system is described in U.S application Ser. No. 08/311,297, filed on Sep. 23, 1994, incorporated herein by reference.

Using such a feedback system, after the RF energy is turned off, the cutting means 11 is advanced and the staples 17 are fired using the firing trigger 14.

Referring now to FIGS. 18–24, there are illustrated alternative electrode configurations of other embodiments of the present invention. The actuation and other instrument features are the same as those illustrated in FIGS. 1–17, with the exception of the location of the electrodes on the end effectors.

Figure 18:
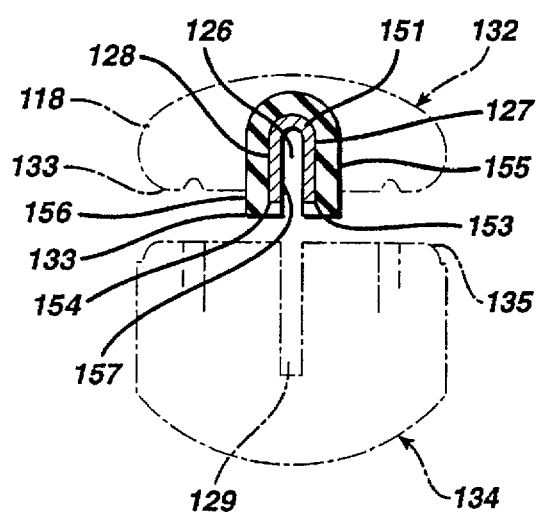
FIG. 18 illustrates a front cross-sectional view of the end effector having an alternative electrode configuration.

Referring to FIG. 18, Jaw member 132 comprises a U-shaped first electrode 151 comprising a first pole, an anvil 118 forming a second and electrically opposite pole, and a U-shaped insulating material 155 surrounding the first electrode 151 except for an exposed portion 157 of the first electrode 151.

The first electrode 151 comprises two electrically communicating electrode bars 127, 128 comprised of an electrically conductive material. The bars 127, 128 are separated by a knife channel 126 which forms a portion of the interfacing surface 133. The insulative material 155 surrounds the outside of the U-shaped electrode and the top portions 153, 154 of the U-shaped electrode 151 so that the electrode is insulated at the inner surface 133 except for the exposed portion 157 of the electrode 151 recessed within the knife channel 126. It is noted that the extent of the recess may vary along the length of the recessed electrode.

The tissue which is squeezed into the recessed portion, the knife channel 126, thereby forms a current path between the recessed exposed portion 157 and the anvil 118.

Jaw member 132 has an inner surface 133 which interfaces with inner surface 135 of jaw 134. The insulative material 155 forms a compression ridge 156 on interfacing surface 133. In use, tissue is engaged and approximated between jaws 132,134. The compression ridge 156 compresses tissue against opposing jaw 134 forming a zone of highly compressed tissue or a compression zone. The recessed exposed portion 157 of the electrode 151 is arranged to be in contact tissue when tissue is compressed in the compression zone. Tissue is compressed into the knife channel 126, so that the tissue is in contact with the recessed exposed electrode portion 157. The tissue is also in contact with the anvil 118.

Figure 19:
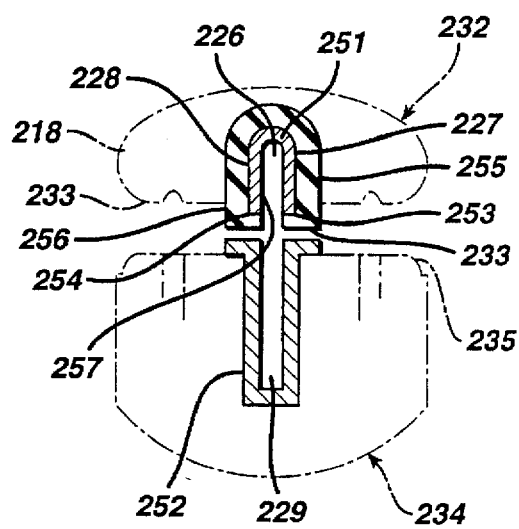
FIG. 19 illustrates a front cross-sectional view of the end effector having an alternative electrode configuration.

Referring to FIG. 19, an alternative end effector electrode configuration is illustrated. Jaw member 232 comprises a U-shaped first electrode 251 comprising a first pole, an anvil 218, and a U-shaped insulating material 255 surrounding the first electrode 251 except for an exposed portion 257 of the first electrode 251.

The first electrode 251 comprises two electrically communicating electrode bars 227, 228. The bars 227,228 are separated by a knife channel 226 which forms a portion of the interfacing surface 233. The insulative material 255 surrounds the outside of the U-shaped electrode and the top portions 253, 254 of the U-shaped electrode 251 so that the electrode is insulated at the inner surface 233 except for the exposed portion 257 of the electrode 251 recessed within the knife channel 226. The insulative material 255 forms a compression ridge 256 on interfacing surface 233.

A second jaw member 234 has an inner surface 235 which interfaces with inner surface 233 of jaw member 232. Jaw member 234 includes a knife channel 229 which is formed by a second electrode 252. The second electrode 252 extends out of the knife channel 229 to interface with insulating material 255 of compression ridge 256. Thus, electrode 251 is offset or recessed from electrode 252.

Figure 20:
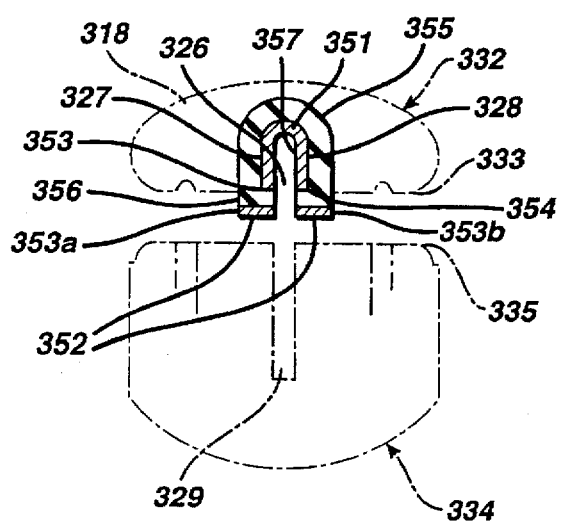
FIG. 20 illustrates a front cross-sectional view of the end effector having an alternative electrode configuration.

Referring now to FIG. 20, there is illustrated an alternative embodiment of an end effector of the present invention. Jaw member 332 comprises a U-shaped first electrode 351 comprising a first pole, an anvil 318, a U-shaped insulating material 355 surrounding the first electrode 351 except for an exposed portion 357 of the first electrode 351, and a pair of second electrodes 352 of an electrically opposite potential from the first electrode 351. The second electrodes 352 are located on ends 353a and 354a of a compression ridge 356 formed by insulating material.

The first electrode 351 comprises two electrically communicating electrode bars 327, 328. The interfacing surface is formed by the anvil 318, electrodes 352, insulating material 355 and electrode 351. The bars 327, 328 are separated by a knife channel 326 which forms a portion of the interfacing surface 333. The insulative material 355 surrounds the outside of the U-shaped electrode and the top portions 353, 354 of the U-shaped electrode 351 so that the electrode is insulated at interfacing surface 333 except for the exposed portion 357 of the electrode 351 recessed within the knife channel 326. A second jaw member 334 has an inner surface 335 which interfaces with inner surface 333 of jaw member 332. Thus, electrode 351 is recessed or is offset from electrodes 352.

Figure 21:
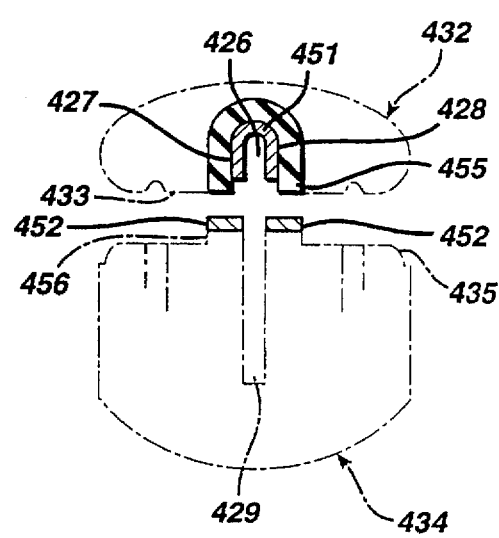
FIG. 21 illustrates a front cross-sectional view of the end effector having an alternative electrode configuration.

Referring now to FIG. 21, there is illustrated an alternative embodiment of an end effector of the present invention. Jaw member 432 comprises a U-shaped first electrode 451 comprising a first pole, an anvil 418, and a U-shaped insulating material 455 surrounding the first electrode 451.

The first electrode 451 comprises two electrically communicating electrode bars 427, 428. The bars 427, 428 are separated by a knife channel 426 which forms a portion of the interfacing surface 433. The electrode 451 is recessed within the knife channel 426.

A second jaw member 434 has an inner surface 435 which interfaces with inner surface 433 of jaw member 432. Jaw member 434 includes a knife channel 429 which is formed by an insulative material. A second electrode 452 is comprised of two bar electrodes 427a, 428a located on interfacing surface 435. The second electrode 452 extends out of the knife channel 429 to form a compression ridge 456 opposed from insulating material 455 and bars 427, 428. Thus, at least a portion of electrode 452 is offset with respect to electrode 451.

Figure 22:
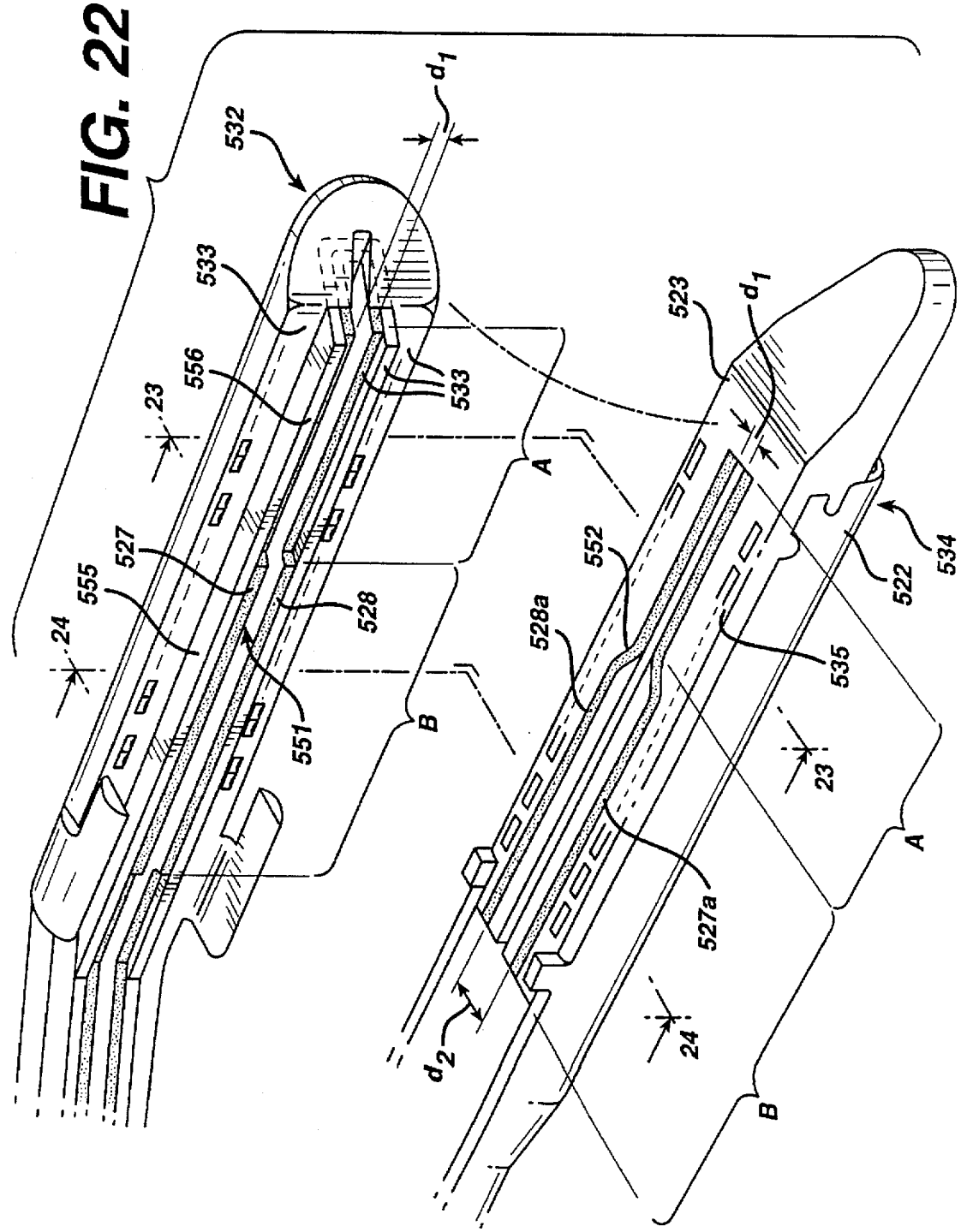
FIG. 22 illustrates a perspective view of the end effector having an alternative electrode configuration.
Figure 23:
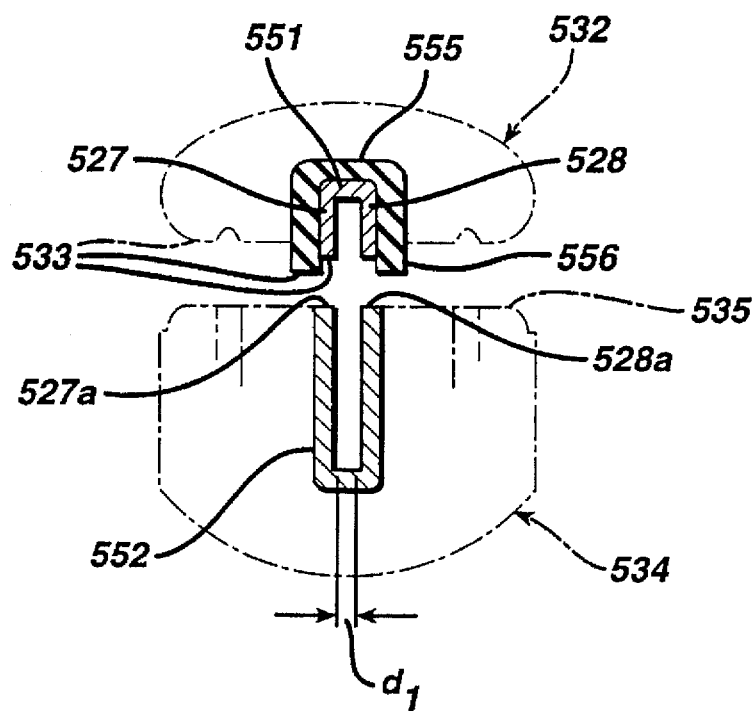
FIG. 23 illustrates a front cross-sectional view of Section A of the end effector of FIG. 22 through lines 23—23.
Figure 24:
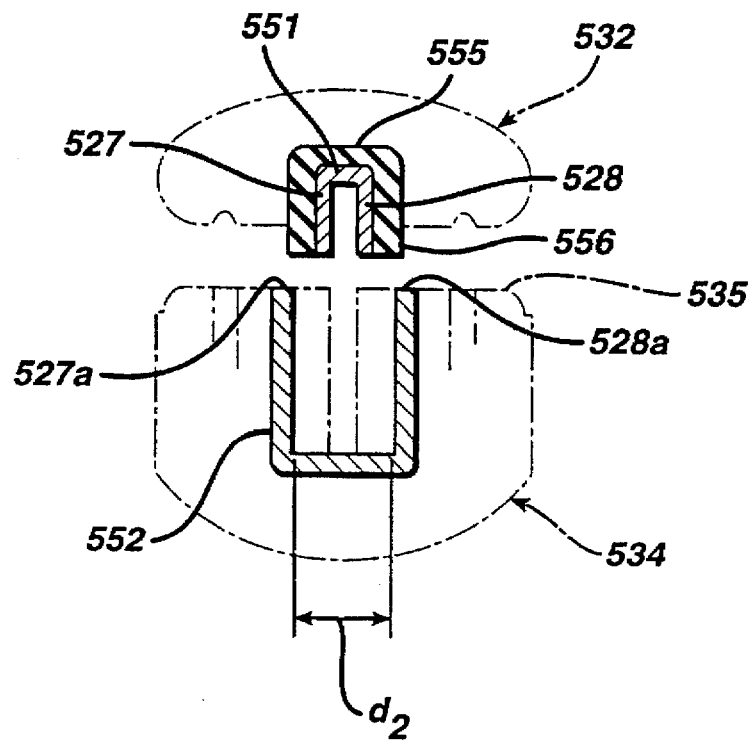
FIG. 24 illustrates a front cross-sectional view of Section B of the end effector of FIG. 22 through lines 24—24.

Referring now to FIGS. 22–24, there is illustrated an alternative embodiment of the end effector of the present invention. The end effector comprises jaw members 532, 534, each of which is divided into two sections, A and B. Jaw member 532 comprises a first electrode 551 of a first pole an anvil 518, and an insulating material 555 surrounding the first electrode 551.

The first electrode 551 comprises two electrically communicating electrode bars 527, 528. A knife channel 526 is located between the bars 527, 528. Insulating material 555 forms a compression ridge 556. In section A, the electrode 551 is recessed within the knife channel 526. In section B, the electrode 551 forms a portion of the compression ridge 556.

Jaw member 534 comprises a staple cartridge 523, a cartridge holder 522, an inner surface 535, and a second electrode 552 of an electrically opposite potential from the first electrode 551. The second electrode 552 is comprised of two electrically communicating electrode bars 527a, 528a. In section A, the bars 527a and 528a are opposed from bars 527 and 528 with respect to the surfaces 532 and 534. In section B, the bars 527a and 528a are offset from bars 527 and 528 with respect to interfacing surfaces. Thus, electrode 551 is either recessed with respect to a plane defined by the compression zone or offset from electrode 552 with respect to interfacing surfaces, so that tissue compression in a compression zone minimizes the opportunity for instrument shorting.

Electrodes 527 and 528 of the jaw member 532 are a distance, $d_1$, from each other. Electrodes 527a and 528a of the cartridge 523 are a distance, $d_1$, from each other in Section A and electrodes 527a, 528a are a distance, $d_2$, from each other in Section B. In this particular embodiment, $d_1 < d_2$. This arrangement provides, among other things, control of thermal spread and coagulation width at the distal end of the instrument. The transition from $d_1$ to $d_2$ may be gradual or stepped, or may occur at various locations along the end effector of the instrument.

Several variations of this invention have been described in connection with specific embodiments involving endoscopic cutting and stapling. Naturally, the invention may be used in numerous applications where hemostasis in desired. Accordingly, it will be understood by those skilled in the art that various changes and modifications may be made in the invention without departing from its scope, which is defined by the following claims and their equivalents.

What is claimed is:

1. An electrosurgical device having an end effector capable of receiving electrosurgical energy therein, said end effector comprising:
    first and second opposing interfacing surfaces, said interfacing surfaces capable of engaging tissue therebetween, at least one of said first and second interfacing surfaces being electrically insulating and including a recessed portion;
    electrically isolated first and second poles comprised of electrically different electrodes capable of conducting electrosurgical energy therethrough, said first pole comprised of a first electrode of a first electrical potential and said second pole comprised of a second electrode of a second electrical potential different from said first potential; and
    wherein said first electrode is located on one of said interfacing surfaces and said second electrode is located on at least one of said interfacing surfaces, and a tissue contacting portion of at least one of said electrodes is located below said interfacing surface on a said recessed portion, said electrodes being arranged so that electrosurgical energy may be communicated between said poles through the tissue.

2. The electrosurgical device of claim 1 wherein a portion of said second interfacing surface comprises a ridge extending from said second interfacing surface to form a tissue compression zone between said interfacing surfaces, said ridge including said recessed portion.

3. The electrosurgical device of claim 2 wherein said first and second electrodes are arranged to provide a current path through tissue in the compression zone.

4. The electrosurgical device of claim 2 wherein a portion of said first interfacing surface comprises a ridge adapted to form said tissue compression zone with said ridge of said second interfacing surface.

5. The electrosurgical device of claim 1 wherein a portion of said second interfacing surface comprises a ridge extending from said second interfacing surface to form a tissue compression zone between said interfacing surfaces, wherein said first interfacing surface includes said recessed portion and wherein said ridge is adapted to compress tissue into said recessed portion to cause the tissue to make electrical contact with said portion of at least one electrode located at said recessed portion.

6. The electrosurgical device of claim 5 wherein said first and second electrodes are arranged to provide a current path through tissue in the compression zone.

7. The electrosurgical device of claim 5 wherein the ridge is formed of an insulator electrically isolating said first electrode from said second electrode.

8. The electrosurgical device of claim 1 wherein at least one electrode of each said pole is located on a same interfacing surface.

9. The electrosurgical device of claim 1 wherein a said second electrode is located on an opposite interfacing surface as a said first electrode.

10. The electrosurgical device of claim 1 wherein said first electrode is arranged in a substantially parallel manner with respect to said second electrode.

11. The electrosurgical device of claim 1 further comprising a longitudinal axis extending proximally to distally with respect to said end effector;
    wherein a said first electrode comprises an elongated electrode extending longitudinally with respect to said axis.

12. The electrosurgical device of claim 1 wherein said device includes a cutting element arranged on said device to divide tissue engaged by said end effector through a cutting line when said cutting element is actuated.

13. The electrosurgical device of claim 12 wherein said end effector further comprises at least one staple and at least one driver adapted to apply said at least one staple lateral to said cutting line.

14. The electrosurgical device of claim 13 wherein said end effector further comprises a channel through which said cutting element is adapted to move, wherein said channel forms said recessed portion.

15. The electrosurgical device of claim 12 wherein said cutting element is movable in a cutting path to form said cutting line.

16. The electrosurgical device of claim 12 wherein the first pole comprises a pair of electrodes between which the cutting element is adapted to move.

17. The electrosurgical device of claim 16 wherein each electrode of said pair of electrodes comprises a substantially parallel elongated bar electrode in electrical communication with the other of said pair of electrodes, and a slot for the cutting element to travel between the bar electrodes.

18. The electrosurgical device of claim 17 wherein said slot forms said recessed portion.

19. The electrosurgical device of claim 12 wherein the end effector is adapted to provide hemostasis of tissue lateral to said cutting line.

20. The electrosurgical device of claim 12 wherein said end effector further comprises at least one fastener and at least one applier adapted to apply said at least one fastener lateral to said cutting line.

21. The electrosurgical device of claim 1 wherein said end effector further comprises:
    at least one fastener and at least one applier adapted to apply said at least one fastener through tissue.

22. The electrosurgical device of claim 1 wherein said end effector further comprises:
    at least one staple and at least one driver adapted to drive said at least one staple through tissue.

23. The electrosurgical device of claim 22
    wherein said device includes a cutting element adapted to divide tissue engaged by said interfacing surfaces; and
    wherein said end effector further comprises: a cartridge containing at least one row of staples, having a slot extending longitudinally therethrough for receiving the cutting element, said slot arranged to permit said cutting element to travel lateral to said at least one row of staples, said cartridge forming the second interfacing surface;
    wherein said at least one driver is adapted to apply said at least one row of staples to tissue engaged by said end effector; and an anvil for receiving and forming said staples, said anvil forming a portion of the first interfacing surface.

24. The electrosurgical device of claim 23 wherein said at least one driver is adapted to apply staples to tissue as the cutting element cuts between the parallel rows.

25. The electrosurgical device of claim 23 wherein a said second electrode is located on said anvil.

26. The electrosurgical device of claim 23 wherein the cartridge is formed of an insulating material.

27. The electrosurgical device of claim 25 wherein a said second electrode is located on the second interfacing surface formed by said cartridge.

28. The electrosurgical device of claim 23 wherein said end effector is adapted to apply bipolar energy to engaged tissue before the cutting element is advanced.

29. An electrosurgical device having an end effector capable of receiving electrosurgical energy therein, said end effector comprising:

first and second opposing interfacing surfaces, said interfacing surfaces capable of engaging tissue therebetween, at least one of said first and second interfacing surfaces being electrically insulating and including a recessed portion;

electrically isolated first and second poles comprised of electrically opposite electrodes capable of conducting bipolar energy therethrough, said first pole comprised of a first electrode of a first electrical potential and said second pole comprised of a second electrode of a second electrical potential;

wherein said first electrode is located on one of said interfacing surfaces and said second electrode is located on at least one of said interfacing surfaces, and wherein a tissue contacting portion of at least one of said electrodes is located below said interfacing surface on a said recessed portion.

30. The electrosurgical device of claim 29 wherein said at least one of said electrodes is located on a said recessed portion on said first interfacing surface, and is offset from the electrically opposite electrode positioned on said second interfacing surface and with respect to said interfacing surfaces.

31. The electrosurgical device of claim 29 wherein a first portion of said at least one of said electrodes is located on a said recessed portion on said first interfacing surface and wherein a second portion of said at least one of said electrodes is offset from the electrically opposite electrode positioned on said second interfacing surface with respect to said interfacing surfaces.

32. The electrosurgical device of claim 31 said electrodes including a length at which said electrodes are not offset from each other with respect to said interfacing surfaces, wherein at least one of said electrodes is recessed in said end effector where said first and second electrodes are not offset from each other.

* * * * *